US009107865B2

United States Patent
Hutchins et al.

(10) Patent No.: US 9,107,865 B2
(45) Date of Patent: Aug. 18, 2015

(54) METHODS FOR PRODUCING OOCYSTS

(75) Inventors: James E. Hutchins, Durham, NC (US); Julius K. Tyczkowski, Cary, NC (US)

(73) Assignee: Zoetis Services LLC, Florham Park, NJ (US)

( * ) Notice: Subject to any disclaimer, the term of this patent is extended or adjusted under 35 U.S.C. 154(b) by 175 days.

(21) Appl. No.: 11/327,026

(22) Filed: Jan. 6, 2006

(65) Prior Publication Data
US 2006/0104996 A1    May 18, 2006

Related U.S. Application Data

(62) Division of application No. 10/232,204, filed on Aug. 29, 2002, now Pat. No. 7,166,290.

(60) Provisional application No. 60/316,310, filed on Aug. 30, 2001.

(51) Int. Cl.
| | | |
|---|---|---|
| *C12N 9/08* | (2006.01) | |
| *C12N 1/00* | (2006.01) | |
| *C12N 1/38* | (2006.01) | |
| *A61K 33/42* | (2006.01) | |
| *A61K 39/012* | (2006.01) | |
| *C12N 1/10* | (2006.01) | |
| *A61K 39/00* | (2006.01) | |

(52) U.S. Cl.
CPC ............... *A61K 39/012* (2013.01); *C12N 1/10* (2013.01); *A61K 2039/52* (2013.01); *Y10T 436/25* (2015.01); *Y10T 436/255* (2015.01); *Y10T 436/25625* (2015.01)

(58) Field of Classification Search
CPC ..... A61K 39/012; A61K 39/52; A61K 45/06; A61K 35/68; A61K 2300/00; A01N 25/22; A01N 37/36; A01N 31/16; A01N 2300/00; C07K 14/44; C07K 14/445; C07K 14/4705; C12Q 1/04; C12Q 2304/00; C12N 1/00; C12N 3/00; C12N 15/74; C11D 39/3945
USPC ........ 424/93.1, 267.1, 271.1; 435/2, 7.32, 30, 435/40.5, 173.1, 173.7, 173.8, 173.9, 242, 435/243, 244, 258.1, 258.4, 344; 530/388.6
See application file for complete search history.

(56) References Cited

U.S. PATENT DOCUMENTS

| | | | |
|---|---|---|---|
| 3,147,186 A | 9/1964 | Edgar | 167/78 |
| 3,617,529 A | 11/1971 | Thompson et al. | 208/230 |
| 3,617,539 A | 11/1971 | Grutsch et al. | 210/13 |
| 3,827,557 A | 8/1974 | Fischer | 209/167 |
| 4,040,388 A | 8/1977 | Miller | 119/1 |
| 4,208,282 A | 6/1980 | Becker | 210/44 |
| 4,301,148 A | 11/1981 | Shibata et al. | 424/93 |
| 4,357,320 A | 11/1982 | Apontowell et al. | 424/89 |
| 4,438,097 A | 3/1984 | Shirley | 424/88 |
| 4,458,630 A | 7/1984 | Sharma et al. | 119/1 |
| 4,469,047 A | 9/1984 | Miller | 119/1 |
| 4,500,638 A | 2/1985 | Apontowell et al. | 435/235 |
| 4,505,892 A | 3/1985 | Apontowell et al. | 424/89 |
| 4,544,548 A | 10/1985 | Davis et al. | 424/93 |
| 4,593,646 A | 6/1986 | Miller et al. | 119/1 |
| 4,639,372 A | 1/1987 | Murray et al. | 424/88 |
| 4,650,676 A | 3/1987 | Schenkel et al. | 424/88 |
| 4,681,063 A | 7/1987 | Hebrank | 119/1 |
| 4,681,682 A | 7/1987 | White et al. | 210/221.2 |
| 4,724,145 A | 2/1988 | Murray et al. | 424/88 |
| 4,735,801 A | 4/1988 | Stocker | 424/92 |
| 4,751,079 A | 6/1988 | Burger et al. | 424/89 |
| 4,790,943 A | 12/1988 | Dunn et al. | 210/705 |
| 4,808,404 A | 2/1989 | Bhogal | 424/88 |
| 4,863,731 A | 9/1989 | Davis et al. | 424/93 |
| 4,913,826 A | 4/1990 | Mannig et al. | 210/707 |
| 4,935,007 A | 6/1990 | Bafundo et al. | 604/49 |
| 5,004,607 A | 4/1991 | Ragland et al. | 424/88 |
| 5,006,341 A | 4/1991 | Davis et al. | 424/442 |
| 5,028,421 A | 7/1991 | Fredericksen et al. | 424/85.2 |
| 5,045,313 A | 9/1991 | Frenkel et al. | 424/88 |
| 5,055,292 A | 10/1991 | McDonald et al. | 424/88 |
| 5,068,104 A | 11/1991 | Bhogal et al. | 424/88 |
| 5,106,617 A | 4/1992 | Federicksen et al. | 424/85.2 |
| 5,279,960 A | 1/1994 | Anderson et al. | 435/243 |
| 5,280,042 A | 1/1994 | Lopes | 514/557 |
| 5,288,845 A | 2/1994 | Chakraborty et al. | 536/24.32 |

(Continued)

FOREIGN PATENT DOCUMENTS

| | | |
|---|---|---|
| CA | 2098773 | 12/1994 |
| EP | 047662 | 12/1987 |

(Continued)

OTHER PUBLICATIONS

Stuart Bibby Scientific Technical Note: T11-001 pH of Distilled Water.*
Waldenstedt et al., "Comparison Between Effects of Standard Feed and Whole Wheat Supplemented Diet on Experimental *Eimeria tenella* and *Eimeria maxima* Infections in Broiler Chickens," *Acta vet. scand.* (1998) vol. 39 (4): pp. 461-471.
"A Cleaning Method for Coccidial Oocysts Using Density-Gradient Sedimentation," *The Journal of Parasitology* 49(1): 159-160.
Bare et al., "Algae removal using dissolved air flotation," *Journal WPCF* 47(1): 153-169 (1975).
Bass, "Uncinariasis in Mississippi," *J. Amer. med. Ass.* 47: 185-187 1906).

(Continued)

*Primary Examiner* — Ja'na Hines
(74) *Attorney, Agent, or Firm* — Barbara L. Renda; Kelly M. Sullivan

(57) ABSTRACT

The present invention provides improved methods and compositions for producing oocysts. The oocysts produced according to the invention find use in the manufacture of vaccines. In preferred embodiments, the present invention provides methods and compositions for the production of *Eimeria* oocysts. Vaccines containing *Eimeria* oocysts, sporocysts and/or sporozoites produced according to the present invention may be used to immunize birds against coccidiosis either in ovo or post hatch.

14 Claims, No Drawings

(56) References Cited

U.S. PATENT DOCUMENTS

| | | | | |
|---|---|---|---|---|
| 5,311,841 | A | 5/1994 | Thaxton | 604/51 |
| 5,339,766 | A | 8/1994 | Phelps et al. | 119/6.8 |
| 5,359,050 | A | 10/1994 | Chakraborty et al. | 536/24.32 |
| 5,661,015 | A * | 8/1997 | Binger et al. | 435/364 |
| 5,674,484 | A | 10/1997 | Miller et al. | 424/93.1 |
| 5,702,612 | A | 12/1997 | Wang | 210/703 |
| 5,807,551 | A | 9/1998 | Reynolds | 424/159.1 |
| 5,843,722 | A | 12/1998 | Bumstead et al. | 435/693 |
| 5,846,527 | A | 12/1998 | Miller et al. | 424/93.1 |
| 5,932,225 | A | 8/1999 | Wallach et al. | 424/267.1 |
| 5,997,911 | A | 12/1999 | Brinton et al. | 424/632 |
| 6,019,985 | A | 2/2000 | Brown et al. | 424/265.1 |
| 6,036,950 | A | 3/2000 | Baker | 424/93.1 |
| 6,106,854 | A * | 8/2000 | Belfer et al. | 424/405 |
| 6,231,871 | B1 | 5/2001 | Coloe | 424/258.1 |
| 6,306,385 | B1 | 10/2001 | Lee | 424/93.1 |
| 6,495,146 | B1 | 12/2002 | Evans et al. | 424/265.1 |
| 2002/0031530 | A1 | 3/2002 | Evans et al. | 424/184.1 |
| 2002/0090378 | A1 | 7/2002 | Evans et al. | 424/267.1 |
| 2002/0146435 | A1 | 10/2002 | Evans et al. | 424/267.1 |

FOREIGN PATENT DOCUMENTS

| | | | |
|---|---|---|---|
| EP | 0 256 878 | 2/1988 | |
| EP | 256878 | 2/1988 | |
| EP | 258045 | 3/1988 | |
| EP | 291173 | 11/1988 | |
| EP | 0 325 359 | 7/1989 | A61K 47/00 |
| EP | 344808 | 12/1989 | |
| EP | 109942 | 3/1991 | |
| EP | 439056 | 7/1991 | |
| EP | 522482 | 1/1993 | |
| EP | 650733 | 5/1995 | |
| EP | 1 036 511 A2 | 8/2001 | |
| JP | 313437 | 12/1989 | |
| JP | 08 268807 | 10/1996 | |
| JP | 08268817 | 10/1996 | |
| JP | H08-268817 * | 10/1996 | A01N 59/00 |
| NL | 8802399 | 4/1990 | |
| RU | 2019189 | 9/1994 | A61K 39/012 |
| WO | WO 9301276 | 1/1993 | |
| WO | WO 9416725 | 8/1994 | |
| WO | WO 96/40233 | 12/1996 | |
| WO | WO 96/40234 | 12/1996 | |
| WO | WO 9640234 | 12/1996 | |
| WO | WO 9712582 | 4/1997 | |
| WO | WO 97/28691 | 8/1997 | |
| WO | WO 9814212 | 4/1998 | |
| WO | WO 98/21305 | 5/1998 | |
| WO | WO 8808699 | 11/1998 | |
| WO | WO 00/50072 * | 8/2000 | A61K 39/00 |
| WO | WO 0134187 | 5/2001 | A61K 39/012 |
| WO | WO 02/37961 | 5/2002 | |

OTHER PUBLICATIONS

Davis, "Techniques" 411-458.
Dulski et al, "The Purification of Sporocysts and Sporozoites from *Eimeria tennella* Oocysts Using Percoll Density Gradients," *Avian Diseases* 32: 235-239 (1988).
Eckert et al., Editors, "Guidelines on techniques in coccidiosis research," *European Commission* 1-24 (1995).
Graat et al., "Rate and course of sporulation of oocysts of *Eimeria vulina* under different environmental conditions," *Parasitology* 108: 497-502 (1994).
Grunnet et al, "Elimination of *Ascaris suum* Eggs from Sewage by Air flotation," *Nord. Vet-Med.* 29: 458-459 (1977).
Hammond et al., "An improved method for sporulating oocysts in bovine faecal material,"*Amer. J. Vet. Res.* 5: 70-71 (1944).
Hill et al., "A mechanical apparatus for screening worm eggs from faeces," *J. Parasit.* 47: 357-362 (1961).
Jackson, "The isolation of viable coccidial sporozoites," *Parasitology* 54: 87-93 (1964).

Jeston et al., "Comparison of the Infectivity of *Eimeria tenella* Oocysts Maintained at 4, 12 or 28° C. Over Time to Determine the Optimal Storage Temperature," *VIIIth International Coccidiosis Conference* (Jul. 2001).
Lane, "The Mass Diagnosis of Ankylostome Infestation (Part I)," *Trans. Roy. Soc. Trop. Med. Hyg.* 16: 274-313 (1923).
Lotze et al., "A practical method for culturing coccidial oocysts in tap water," *J. Parasit.* 47:.5880590 (1961).
Marquardt et al, "The Effect of Physical and Chemical Agents on the Oocyst of *Eimeria zurnii* (Protozoa, Coccidia)," *J. Protozool* 7(2): 186-189 (1960).
Marquardt, "Separation of Nematode Eggs from Fecal Debris by Gradient Centrifugation," *The Journal of Parasitology* 248-250.
Nyberg et al., "Effect of Sodium Hypochlorite on the Oocyst Wall of *Eimeria tenella* as Shown by Electron Microscopy," *Proceedings of the Helminthological Society of Washington* 37(1): 32-36 (1970).
Patnaik, "A Technique of Obtaining Oocysts of Coccidia in Pure State from Chicken Faeces by Modified Marquardt's Method," *The Indian Veterinary Journal* 414-422.
Peterson et al., "Replacement of the Medium for a Natural Phytoplankton Community by Tangential-Flow Filtration, with Special Emphasis on Toxicity Tests," *Bull. Environ. Contam. Toxicol.* 57: 603-609 (1996).
Ryley et al., "Methods in coccidiosis research: separation of oocysts from faeces," *Parasitology* 73: 311-326 (1976).
Schmatz et al., "Purification of *Eimeria* Sporozoites by DE-52 Anion Exchange Chromatography," *J. Protozool* 31(1): 181-183 1984).
Smith et al., "Froth Flotation for Harvesting *Chlorella* Algae," *Northwest Science* 42(4): 165-171 (1968).
Vetterling, "Continuous-flow Differential Density Flotation of Coccidial Oocysts and a Comparison with Other Methods," *The Journal of Parasitology* 55(2): 412-417 (1969).
Whitlock, "The recovery and identification of the first-stage larvae of sheep nematodes," *Aust. vet. J.* 35: 310-316 (1959).
Wilson et al., "Biochemistry of Sproulation in Oocysts of *Eimeria acervulina,"* Biochemistry of Sporulation 8(4): 410-416 (1961).
*International Search Report*, PCT/US02/27668: (Date of Mailing: Jan. 13, 2003).
Jeffers, et al., *Embryonic Response to Eimeria tenella Infection* J. Parisitol., 56(4), 1970, 656-662.
Fredericksen, et al., *In Ovo Administration of a Potential Recombinant Coccidial Antigen Vaccine in Poultry* Les Colloques De L'Inra, 49, 1989, 655-660.
Proceedings of the VI$_{th}$ International Coccidosis Conference, Jun. 21-25, 1993, Guelph, Ontario, Canada. Univ. of Guelph; p. 103. Vaccine Symposium Papers.
Sharma & Burmester, *Resistance to Marek's Disease at Hatching in Chickens Vaccinated as Embryos With Turkey Herpesvirus* Avian Diseases, 26(1), 134-148.
Schmatz, etal., *Purification of Eimeria Sporozoites by DE-SZ Anion Exchange Chromatography J. Protozool..* 31(1), 1984, 181-183.
Stedman'S Medical Dictionary, 25$^{th}$ Ed., 1990, p. 947, 1087, 1457 and 1458.
Ruff, et al., Poultry Science, 1988, 67 (Supplement I):147.
Shirley; Live Vaccines for the Control of Coccidiosis; VIth International Coccidiosis Conference, p. 61-72 (1993).
Shirley; Development of a Live Attenuated Vaccine Against Coccidiosis of Poultry; Parasite Immunology; p. 117-124 (1989).
Watkins, et al.; The Effect of In Ovo Oocyst or Sporocyst Inoculation on Subsequent Coccidial Challenge; VLth. International Coccidiosis Conference Abstract EL-2. Ontario, Canada (1993), Poultry Science 1597-1602 (1995).
R. B. Williams; The Development, Efficacy and Epidemiological Aspects of Paracox\m, A New Coccidiosis Vaccine for Chickens; Mallinckrodt Veterinary Ltd: pp. 1-16 (1992).
Your Questions Answered; Live Attenuated Oral Coccidiosis Vaccine; Paracox, Cocci Vac® Vaccines, Cocci Vac®-T,Cocivac®-D, Cocci Vac®-B, Bursa-Vac®, Bursa-Vac®-3 and Bursa-Vac®-4; Mallinckrodt Veterinary.
The Headlines of the 80's . . . Immucox; Coccivac Brand of Coccidiosis Vaccines; Mallinckrodt Veterinary; pp. 1-11.

(56) References Cited

OTHER PUBLICATIONS

Immucox Coccidiosis Vaccine the Natural Solution; AAP Tek Ingredients, A Divisional of Ontario Limited: pp. 1-6.

M. W. Shirley, et al.; Live Attenuated Vaccines Against Avia Coccidiosis; Parasitology Today; vol. 13 No. 12 pp. 481-484 (1997).

Ahmad, J. et al. Evaluation of a Modified-Live Virus Vaccine Administered In Ovo to Protect Chickens Against Newcastle Disease *Am. J. Vet. Res.* 153(11): 1999-2001.

Hosek, et al., *Improved Method For High-Yield Exystation and Purification of Infective Sporozoites of Eimeria Spp.* J. Protozool 35(4), 1988, 583-589.

Olson, *In Situ Enzyme-Linked Immunosorbent Assay to Quantitative In Vitro Development of Eimeria tenella* Antimicrob. Agents Chemother 34(7), Jul. 1990, 1435-39.

Perkins, Microscopic Anatomy of Invertebrates vol. 1: Protozoa, Chap. 4: "Sporozoa" 261-331, 1991. Wiley-Liss.

Proceedings of the VIth International Coccidosis Conference, Jun. 21-25, 1993, Guelph, Ontario, Canada, Univ. of Guelph; p. 105-128, Vaccine Symposium Papers.

Fuller et al., "Analysis of Coccidian Oocyst Populations by Means of Flow Cytometry," *J. Protozool.* 36(32): 143-146 (1989).

O'Grady et al., "An Investigation of Variables in an Fecal Flotation Technique," *Can. J. comp. Med.* 44: 148-154 (Apr. 1980).

\* cited by examiner

US 9,107,865 B2

METHODS FOR PRODUCING OOCYSTS

RELATED APPLICATION INFORMATION

This application is a divisional of U.S. application Ser. No. 10/232,204 filed Aug. 29, 2002 (allowed) now U.S. Pat. No. 7,166,290, which claims the benefit of U.S. Provisional Application Ser. No. 60/316,310 filed Aug. 30, 2001, the disclosures of which are incorporated by reference herein in their entireties.

FIELD OF THE INVENTION

The present invention provides methods and compositions for the production of oocysts from protozoa; in particular, the present invention provides methods and compositions for the production of *Eimeria* oocysts.

BACKGROUND OF THE INVENTION

Coccidiosis of poultry is a disease caused by protozoan parasites of the genus *Eimeria*. Oocysts of *Eimeria* species are ubiquitous in the environment and persist for many months in poultry litter. Ingestion of oocysts leads to infection of the various regions of the intestinal tract in a species-specific manner. The organism proliferates in the intestine over a period of several days, resulting in the excretion of the next generation of oocysts in the feces. Multiple cycles of infection lead to immunity, and when the infection is presented to a flock early and in a uniform dosage among the flock, the immunity developed over several cycles of exposure can be quite robust.

In contrast, when birds are not presented with the infection in a uniform manner, situations may arise in which naïve birds are subject to sudden, massive infection, leading to poor performance in terms of feed conversion and weight gain, and a high risk of secondary infections. Currently, the most common method used for control of coccidiosis in the poultry industry is not vaccination, but rather the administration of anticoccidial drugs in the feed. The low rate of vaccination is often attributed to uncertainty in the uniformity in dosing via the feed or water at the growout facility or by spray cabinet vaccination at the hatchery, which are the traditional routes and times of administration. There is increasing interest in improving the uniformity of delivery during administration at the hatchery.

Recently, in ovo vaccination techniques have been found applicable to administration of a live oocyst-based coccidiosis vaccine (WO 96/40234 and WO 96/40233; Pfizer, Inc.). The in ovo route of administration provides a convenient method of delivering a uniform dose of vaccine to each embryo while it is still in the egg. Delivery of avian vaccines in ovo is currently practiced for approximately 85% of the 9 billion broiler birds produced in the United States each year and in a growing percentage of the 21 billion broiler birds produced outside of the United States each year (see, e.g., U.S. Pat. No. 4,458,630). Therefore, the potential market for a live, in ovo-delivered coccidiosis vaccine is considerably larger than the current market for post hatch-delivered coccidiosis vaccines.

Oocysts for use in a live coccidiosis vaccine are derived from chicken feces which are initially heavily laden with contaminating microorganisms. Typically, regulatory agencies require that in ovo-delivered vaccines be shown to be essentially free of contaminating microorganisms. To most completely ensure that bioburden levels are fully minimized in the final product, it is beneficial to use compositions and methodologies which effectively control the level of contaminating microorganisms at each stage of the oocyst production process, including the collection and sporulation processes as well as the sanitization process.

Current methods of producing oocysts for vaccine manufacture may suffer from a drawback in that they frequently utilize materials that are biohazardous or corrosive to equipment. Accordingly, there is a need in the art for improved methods of producing oocysts from protozoa, especially for use in vaccine manufacture.

SUMMARY OF THE INVENTION

The present invention relates to improved methods and compositions for producing protozoan oocysts (e.g., *Eimeria*), for example, for use in the manufacture of vaccines. With particular respect to poultry vaccines, the invention is suitable for producing vaccines for post hatch or in ovo use. Likewise, the vaccine may be used in the broiler, laying, breeder, turkey, hobbyist and/or domesticated bird industries.

Accordingly, as a first aspect, the present invention provides a composition for the production of oocysts comprising a peroxygen compound and an organic acid, said composition having an acidic pH. The composition may be used for the collection, sporulation and/or sanitization of protozoan oocysts.

Thus, as a further aspect, the present invention provides a method of collecting protozoan oocysts in animal feces comprising the steps of: (a) providing an animal infected with a protozoan, wherein the animal is shedding oocysts from the protozoan in its feces, and (b) contacting feces comprising oocysts from the infected animal with the composition comprising a peroxygen compound and organic acid.

In particular embodiments of the foregoing, either the peroxygen compound or the organic acid(s) is omitted from the composition, in particular, when used as a collection medium.

As yet a further aspect, the present invention provides a method of sporulating protozoan oocysts, comprising the steps of: (a) providing a composition comprising protozoan oocysts, and (b) sporulating the oocysts in the composition comprising a peroxygen compound and organic acid for a time and under conditions suitable for sporulation.

As still a further aspect, the invention provides a method of sanitizing protozoan oocysts, comprising: (a) providing a preparation comprising protozoan oocysts, and (b) sanitizing the oocysts in the composition comprising a peroxygen compound and organic acid for a time and under conditions sufficient to achieve the desired level of sanitization of the preparation.

As yet another aspect, the present invention provides a flotation medium for purifying protozoan oocysts, comprising a high-density, non-ionic solution and a polycation. In other embodiments, the invention provides a flotation medium for purifying protozoan oocysts, comprising a high-density, non-ionic solution and oil.

The invention also provides methods of purifying protozoan oocysts by flotation, comprising the steps of: (a) forming a suspension between a flotation medium as described above and a plurality of protozoan oocysts, (b) allowing the suspension to separate, and (c) recovering protozoan oocysts from the separated suspension.

In particular embodiments of the foregoing aspects of the invention, the protozoan comprises a species of *Eimeria* and the animal subject is a bird.

As still yet another aspect, the present invention provides a method of producing protozoan oocysts from an avian subject, comprising the steps of: (a) infecting an avian subject with a protozoan for a time sufficient for oocysts from the protozoan to be shed in the feces of the infected avian subject, (b) collecting the feces comprising the oocysts from the infected avian subject, and (c) feeding the infected avian subject a diet having a large mean particle size for at least about 1 day prior to and during at least a portion of said collecting step. In particular embodiments, the protozoan comprises a species from the genus *Eimeria*.

The foregoing and other aspects of the present invention are explained in more detail in the description set forth below.

DETAILED DESCRIPTION OF THE INVENTION

The present invention will now be described with reference to preferred embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

The present invention is suitable for both medical and veterinary uses. The terms "animal" and "animal subjects," include but are not limited to, mammalian and avian subjects, preferably avian subjects.

Suitable mammalian subjects include but are not limited to human, simian, porcine, bovine, caprine, equine, feline, ovine, canine, murine and lagamorph subjects.

The terms "avian" and "avian subjects" or "bird" and "bird subjects" as used herein, are intended to include males and females of any avian or bird species, but are primarily intended to encompass poultry which are commercially raised for eggs, meat or as pets. Accordingly, the terms "avian" and "avian subject" or "bird" and "bird subject" are particularly intended to encompass chickens, turkeys, ducks, geese, quail, pheasant, parakeets, parrots, cockatoo, cockatiel, ostrich, emu and the like. Chickens and turkeys are the preferred avian or bird subjects, with chickens being most preferred.

The present invention relates generally to methods and compositions for the production of oocysts from protozoa. Such methods and compositions find use, e.g., in methods of manufacturing vaccines. Many protozoa form a life stage designated as an "oocyst." The invention can be practiced to produce oocysts from any species of protozoa, including but not limited to *Eimeria, Cryptosporidium, Toxoplasma, Plasmodia* and *Isospora*. In embodiments of the invention, the invention is used to produce *Eimeria* oocysts.

The terms "protozoa", "oocyst", "sporocyst", "sporozoite" and "merozoite" have their accepted meaning in the art. Unless indicated otherwise, these terms are intended to refer to live protozoa, oocysts, sporocysts, sporozoites and merozoites, although those skilled in the art will appreciate that vaccines may be formulated using killed (or attenuated) protozoa, oocysts, sporocysts, sporozoites and merozoites.

The term "*Eimeria*" means one or more species of the genus *Eimeria*. Such *Eimeria* species include those that are found in chickens, including *E. tenella, E. acervulina, E. maxima, E. necatrix, E. mitis, E. praecox, E. mivati* and *E. brunetti*, and also those that are found in turkeys, including *E. meleagrimitis, E. adenoeides, E. gallopavonis, E. dispersa, E. innocua,* and *E. subrotunda*. The term "*Eimeria*" also includes strains or species of *Eimeria* that infect other bird or mammalian species. In addition, the term "*Eimeria*" includes all strains of the foregoing species of *Eimeria*, including but not limited to wildtype strains, precocious or otherwise selected strains, attenuated strains, and oocysts that have been attenuated, e.g., by irradiation, chemical treatment and the like. Further, the term "*Eimeria*" also includes any newly-discovered strains or species of *Eimeria*. Finally, the term "*Eimeria*" encompasses live and killed *Eimeria*, although live *Eimeria* are intended unless indicated otherwise.

Compositions comprising *Eimeria* oocysts find use in methods of immunizing birds against coccidiosis. Methods of vaccinating birds against coccidiosis are known in the art, and include in ovo (e.g., international patent publications WO 96/40234 and WO 96 40233; Pfizer Inc.) and post hatch (e.g., U.S. Pat. No. 3,147,186 to Edgar; U.S. Pat. No. 5,055,292 to McDonald et al.; and U.S. Pat. No. 4,438,097 to Shirley et al.) vaccination methods.

Those skilled in the art will appreciate that oocysts may be further processed to release other life stages (e.g., sporozoites or sporocysts) for use in the final vaccine composition, or to produce protozoal proteins for vaccination purposes.

Likewise, the term "protozoa" includes wildtype strains, precocious or otherwise selected strains, attenuated strains, and oocysts that have been attenuated, e.g., by irradiation, chemical treatment and the like. Further, the term "protozoa" also includes any newly-discovered strains or species of protozoans. Finally, the term "protozoa" covers both live and killed protozoa, although live protozoa are intended unless indicated otherwise.

The terms "produce", "producing" or "production" of oocysts, and the like, encompass the steps of infecting an animal (e.g., a bird) and collecting feces containing oocysts therefrom, sporulating, purifying, and/or sanitizing the oocysts, and the like. Thus, the terms "produce", "producing" or "production" refer to the entire process of harvesting oocysts from an animal and purifying the oocysts from the fecal material or to the individual steps (or a subset of steps) in the process.

Unless indicated otherwise, the terms "purify(ies)," "purification," "purifying," and "purified" as used herein with respect to preparations of oocysts refer to the separation from, or removal of, debris and other unwanted material from preparations containing the oocysts. These terms are intended to indicate that the degree of isolation or separation of the oocysts from other material present in the feces is enhanced, not that absolutely all extraneous materials are removed from the oocyst preparations. Likewise, the oocyst preparation may contain some degree of microbial contamination, as long as the final preparation is suitable for its intended use (e.g., as a vaccine). In the case of vaccines intended for in ovo administration to birds, in particular embodiments, the preparation will be essentially free of detectable contamination by microorganisms, in particular, microorganisms that are pathogenic (i.e., cause significant illness or mortality) to the embryo.

Depending upon context, a "purification" process may refer to the entire process of purifying oocysts from feces to produce a preparation suitable for vaccination purposes. Alternatively, a "purification" process may refer to any subset of steps, or even a single step, within the entire purification scheme.

The present invention provides methods and compositions for producing oocysts (e.g., *Eimeria* oocysts). The oocysts that are produced are generally of sufficient infectivity, viability and purity for the manufacture of an immunogenic composition for use in vaccination. The methods and compositions of the invention may be used in conjunction with other methods known in the art. Likewise, the various methods and compositions of the invention may be used singly or in combination with each other.

Methods of producing oocysts, such as *Eimeria* oocysts, are known in the art (see, e.g., U.S. Pat. No. 3,147,186 to Edgar; U.S. Pat. Nos. 4,544,548 and 4,863,731 to Davis et al., international patent publication WO 00/50072 (Pfizer, Inc.), and international patent publication WO 02/37961 (Novus International, Inc.); Hammond et al., (1944) *Amer. J. Vet. Res.* 5:70; Hill et al., (1961) *J. Parasit.* 47:357; Jackson, (1964) *Parasitology* 54:87; Lotze et al., (1961) *J. Parasit.* 47:588; Schmatzetal., (1984) *J. Protozool.* 31:181; Whitlock, (1959) *Aust. Vet. J.* 35:310. In general, these methods involve infecting an animal with the protozoan of interest, collecting feces that contain oocysts from the infected animal, purifying the oocysts from the fecal material through a series of separation procedures such as sieving, centrifugation, filtration and/or density flotation, sporulating the oocysts, optional additional separation steps, and, optionally, sanitizing the sporulated oocysts to inactivate contaminating microorganisms (including bacteria, mold, fungi, yeast and viruses). Different oocyst preparations (e.g., from different species or strains) may be combined to form a final product, for example, a vaccine against multiple protozoan (e.g., *Eimeria*) species.

The terms "microbial contamination" or "contamination by microorganisms" are intended to indicate the presence of detectable and unwanted viable microorganisms including but not limited to bacteria, molds, fungi, yeast and viruses. In particular embodiments, the oocyst preparation is essentially free of detectable microbial contamination, meaning that no significant levels of microbial contamination are detected in the preparation.

The abbreviation "v/v" refers to "volume/volume." Likewise, the abbreviation "w/v" refers to "weight/volume."

Individual aspects of the present invention are described in more detail below.

Immunogenic Compositions.

Immunogenic compositions produced using the methods of the present invention may be administered to an animal subject to vaccinate against a protozoan disease. An immunogenic composition (e.g., a vaccine) containing oocysts produced using the methods of the present invention may be administered to elicit an immunogenic response. Typically, the immunogenic composition comprises an immunogenic amount of oocysts as disclosed herein in combination with a pharmaceutically-acceptable carrier. An "immunogenic amount" is an amount of the oocysts that is sufficient to initiate or evoke an immune response in the subject to which the immunogenic composition is administered. As understood by those skilled in the art, the immunogenic composition may be formulated with live, attenuated and/or killed organisms. In the case of an in ovo delivered live coccidiosis vaccine, the amount of oocysts is generally sufficient to yield a relatively low level initial infection, which is then followed by multiple rounds of re-infection, via recycling, ultimately leading to immunity. The foregoing discussion is directed to oocysts, but is also applicable to other life forms, such as sporozoites or sporocysts.

By "pharmaceutically acceptable" it is meant a material that is not biologically or otherwise undesirable, i.e., the material may be administered to a subject without causing any undesirable biological effects. Thus, such a pharmaceutical composition may be used, for example, to prepare compositions for immunization. Physiologically and pharmaceutically acceptable carriers may contain other compounds including but not limited to stabilizers, salts, buffers, adjuvants and/or preservatives (e.g., antibacterial, antifungal and antiviral agents) as is known in the art. The pharmaceutically acceptable carrier need not be sterile, although it generally will be for in ovo administration to avian embryos.

Any route of administration of the immunogenic composition known in the art may be employed as long as an active immune response (preferably, a protective immune response) against the protozoa is elicited. When the subject is a bird, the immunogenic composition may be administered in ovo or post-hatch. Exemplary routes of administration are post-hatch oral administration or in ovo injection into the amnion. In particular embodiments of the invention, in ovo administration using automated injection equipment is employed.

The terms "vaccination" or "immunization" are well-understood in the art. For example, the terms vaccination or immunization can be understood to be a process that increases a subject's immune reaction to antigen, and therefore its ability to resist or overcome infection. In ovo methods of vaccinating birds against *Eimeria* are known in the art (e.g., international patent publications WO 96/40234 and WO 96 40233; Pfizer, Inc.).

The terms "protective immunity" or "protective immune response," as used herein, are intended to mean that the host animal mounts an active immune response to the vaccine, such that upon subsequent exposure or a challenge, the animal is able to combat the infection. Thus, a protective immune response will decrease the incidence of morbidity and mortality from subsequent exposure to the pathogen among treated animals. Those skilled in the art will understand that in a commercial animal husbandry setting, the production of a protective immune response may be assessed by evaluating the effects of vaccination on the flock or herd as a whole, e.g., there may still be signs of illness or of morbidity and mortality in a minority of vaccinated animals.

By "active immune response", it is meant any level of protection from subsequent exposure to the protozoan or protozoan antigens which is of some benefit in a population of subjects, whether in the form of decreased mortality, decreased lesions, improved feed conversion ratios, or the reduction of any other detrimental effect of the disease, and the like, regardless of whether the protection is partial or complete. An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection, or as in the present case, by vaccination. Active immunity can be contrasted with passive immunity, which is acquired through the "transfer of preformed substances (antibody, transfer factor, thymic graft, interleukin-2) from an actively immunized host to a non-immune host." Id.

Collection and Sporulation of Oocysts.

Oocysts are typically collected in feces from infected animals and then sporulated in the presence of oxygen prior to attaining infectivity. According to many conventional methods, oocysts are collected and sporulated in a solution containing 2.5% potassium dichromate. Potassium dichromate acts as an antimicrobial solution and as a source of oxygen for oocyst sporulation. However, potassium dichromate is a hazardous material and requires special disposal as hazardous waste. According to conventional methods, the potassium dichromate is removed from the oocyst preparation to produce a final product that is essentially free of this hazardous compound.

According to prior art methods, feces containing oocysts may be collected dry or in a fluid medium containing potassium dichromate during the peak output period for each species (e.g., from about three, four or five days to about six to nine days post-inoculation for *Eimeria* species). After the collection period, the oocysts are then subjected to initial separation from fecal debris using techniques such as sieving or density flotation, and then placed in fresh potassium dichromate medium, stirred, and aerated for 48 to 72 hours to enhance the sporulation process.

In U.S. Pat. No. 3,147,186 to Edgar, sporulation of *Eimeria* oocysts using 1% to 4% potassium dichromate as a sporulation medium is described. This patent states that "[t]his compound serves the several purposes of acting as an antibacterial, antifungal, and antiviral agent and of also supplying oxygen to the oocysts during and after sporulation so as to help preserve their viability." (Col. 11, lines 47-50).

Ryley, et al., (1976) *Parisitology* 73(3):311-326), describes the use of a 2.5% potassium dichromate solutions as a collection, sporulation, and long-term storage medium.

Cost 89/820, Biotechnology, Guidelines on techniques in coccidiosis research. Eckert, J., R. Braun, M. W. Shirley, and P. Coudert, editors. 1995. European Commission, directorate-General XII, Science, Research and Development, Agriculture Biotechnology, Luxembourg. p. 8. also describes the use of 2.5% potassium dichromate in oocyst production.

The present invention provides a medium for collecting oocysts, the collection medium comprising a peroxygen compound and an organic acid. The collection medium will preferably have an acidic pH (e.g., less than about pH 7, 6, 5, 4 or 3) for controlling the growth of unwanted microorganisms and may contain other anti-microbial compounds as well. In particular embodiments, the pH of the collection medium is in the range of about pH 1 to about pH 3.

Oocysts may be collected from feces, cecal cores, intestinal linings, and the like from infected animals. For commercial purposes, however, the oocysts will typically be collected in the feces. The feces are contacted with the collection medium, which may serve one or more purposes, e.g., it may have antimicrobial (e.g., anti-bacterial, anti-fungal, anti-viral, and the like) properties and/or may provide oxygen to maintain the viability of the oocysts. The oxygen in the collection medium may also induce sporulation during the collection period and may shorten or even eliminate a separate sporulation step.

By "collecting" or "collection of" of feces or oocysts in the inventive collection media, it is not necessary that the feces/oocysts be collected directly into the collection medium. The feces/oocysts may be collected "dry" and then transferred into the collection medium of the invention. In embodiments of the invention, the feces/oocysts are transferred to the inventive collection medium within about 0.25, 0.5, 1, 2, 4, 12, 24, 36 or 48 hours after fecal production. In illustrative embodiments, the feces containing the oocysts are caught on a moving belt or sloped surface and then transferred into a collection vessel containing a collection medium of the invention. The feces may be sprayed with collection medium during the transfer (i.e., on the conveyer belt or sloped surface) to the collection vessel.

The ratio of feces to collection medium is not critical as long as it is sufficient to control microbial growth and, if desired, initiate the sporulation process. Exemplary ratios of feces to collection medium are about 1:0.25, about 1:0.5, about 1:1, about 1:2, about 1:3, about 1:4, about 1:5, or about 1:10 (v/v).

Any peroxygen compound known in the art may be used in the collection medium. Exemplary compounds include hydrogen peroxide, sodium perborate (e.g., the monohydrate or tetrahydrate form), sodium percarbonate, magnesium peroxide, calcium peroxide, zinc peroxide, urea peroxide, and a combination thereof. Peroxide compounds may be used with or without an activator such as tetra-acetylethylenediamine (TAED). TAED is typically used at a concentration of about 1-3%.

The peroxygen compound is included in the collection medium at a concentration sufficient to achieve the intended effect (e.g., antimicrobial action and/or sporulation), but insufficient to cause undue damage to the oocysts. The concentration of the peroxygen compound may be as low as about 0.05, 0.1, 0.25, 0.5 or 1% (v/v) or (w/v) and as high as about 0.5%, 1%, 3%, 5%, 10%, 15% (v/v) or (w/v) or more. When the peroxygen compound is hydrogen peroxide, the concentration in the medium is typically from about 0.1%, 0.25% or 0.5% (v/v) to about 1%, 3% or 5% (v/v).

The organic acid may be any organic acid known in the art, including citric acid, acetic acid, propionic acid, or any other mono- or poly-acetic acids, or a combination thereof. The concentration of the organic acid in the medium may be about 0.1%, 0.5%, 1%, 2%, 3%, 5%, 8% or 10% (v/v) or (w/v), or higher. The concentration of the organic acid may further be less than about 25%, 20%, 15%, 12%, 10% (v/v) or (w/v), or less. In particular embodiments, the organic acid is included at a concentration of about 1-15% or about 3-10% (v/v) or (w/v).

In other particular embodiments, in addition to the peroxygen compound, the composition contains from about 1% to about 20% or from about 2.5% to about 10% or 15% citric acid and from about 0.05% to about 1% or from about 0.1% to about 0.5% propionic acid.

The collection medium may additionally contain other components, including buffers, salts, anti-microbial agents and the like. In particular embodiments of the invention, an anti-foaming agent is included. Anti-foaming agents may advantageously be used to reduce foaming and clumping of the oocysts.

As will be appreciated in the art, organic acids may be relatively expensive. Thus, in certain embodiments the organic acid(s) may be omitted from the collection medium.

Likewise, there are certain circumstances in which it may be desirable to avoid the use of the peroxygen compound at the collection stage. Thus, in particular embodiments of the invention, the peroxygen compound is omitted from the collection medium.

In particular embodiments, a peroxygen compound and/or organic acid(s) may be used in connection with a more traditional collection or sporulation medium containing potassium dichromate. In other particular embodiments, the collection and sporulation media of the invention do not contain potassium dichromate and may be safer to use and easier to dispose of than media containing potassium dichromate.

The inventive peroxygen medium comprising a peroxygen compound and an organic acid (each as described above) may alternatively, or additionally, be used as a sporulation medium. The present inventors have found that when the peroxygen medium is used as a collection medium, a significant percentage of *Eimeria* oocysts are sporulated during the collection period. In particular embodiments, at least about 40%, 50%, 60%, 70%, 80%, 85%, 90%, 95, 98% or more of the oocysts are sporulated during the collection period (i.e., prior to any purification steps).

In some embodiments, the peroxygen medium is used as a sporulation medium in a separate sporulation step to complete the sporulation process. Moreover, if the inventive collection medium is not employed (for example, if a potassium dichromate collection medium is used), it is likely that a designated sporulation step will be performed to achieve sufficient sporulation of the oocyst preparation.

Accordingly, in particular embodiments, the present invention provides a method of sporulating oocysts (e.g., *Eimeria* oocysts), comprising the steps of providing a composition comprising oocysts, and sporulating the oocysts in a sporulation medium of the invention for a time and under conditions suitable for sporulation.

In carrying out sporulation after the collection period, the feces are typically collected from the animal, and then optionally subjected to purification steps such as sieving, filtration and the like. The oocysts are then transferred to the sporulation medium, and sporulation is generally allowed to proceed for about 24-96 hours, e.g., for about 48-72 hours under appropriate conditions. For example, the solution may be stirred or agitated and aerated during the sporulation process.

While the peroxygen medium need not be changed between the collection and sporulation processes, for commercial manufacturing purposes, there will generally be one or more intervening purification steps and fresh sporulation medium will be added prior to the sporulation step.

In other embodiments, the sporulation process is carried out concurrently with the collection and/or sanitization (described below) process.

The ratio of solids to collection medium is not critical as long as it is sufficient to achieve the desired level of sporulation and to control microbial growth. Exemplary ratios of feces to collection medium are about 1:0.25, about 1:0.5, about 1:1, about 1:2, about 1:3, about 1:4, about 1:5, or about 1:10 (v/v).

For example, in one illustrative embodiment, feces containing the oocysts are collected in the inventive collection/sporulation medium. The oocysts are purified from the fecal material using sieving, density flotation and/or filtration techniques. The oocysts are then pelleted by centrifugation and resuspended in fresh collection/sporulation medium, and sporulation is allowed to proceed under appropriate conditions (e.g., stirring and/or aeration) for about 48-72 hours.

The sporulated protozoa may then optionally be subjected to additional purification procedures and/or sanitization (described below).

Use of the inventive medium as a collection and/or sporulation medium may be advantageous in that it may protect the oocysts from drying out, reduce the bioburden from the start of the collection period, provide high sporulation rates, and may be more easily disposed of than conventional media containing potassium dichromate.

Following sporulation, steps may be taken to remove the peroxygen compound, e.g., using an enzymatic process, dialysis and/or filtration. For example, the peroxygen compound may be removed using catalytic decomposition (e.g., an enzymatic process or chemical treatment such as with manganese dioxide), dialysis and/or filtration. In the case of hydrogen peroxide, catalase may be used to reduce or remove residual hydrogen peroxide.

Sanitization of Oocysts.

A sanitization step is an optional step that will typically be employed in methods of producing oocysts for in ovo vaccines and is sometimes used for post hatch vaccines as well. As known in the art, oocysts for use in vaccine preparations are conventionally sanitized using sodium hypochlorite solutions, which may cause damage to the oocyst wall, weakening the structure of the oocyst and potentially reducing the long-term viability of the sanitized oocysts during storage.

Vefterling, J. M. ((1969) *J. Parasitology* 55(2):412-417) describes the production of sterile oocysts using hypochlorite medium.

Jackson, A. R. B. ((1964) *Parisitology* 54:87-93) also describes the isolation of viable coccidial sporozoites using hypochlorite as a sanitizing medium.

Nyberg and Knapp ((1970) Proceeding of the Helminthological Society of Washington 37:32-36) describe the effect of sodium hypochlorite on the oocyst wall of *Eimeria* tenella as shown by electron microscopy.

The present inventors have found that the collection/sporulation medium described above comprising a peroxygen compound and organic acid may also be employed as a (sterile) sanitization medium. In particular embodiments, the sanitization medium will further comprise hypochlorite (i.e., bleach) or other sanitizing agents known in the art.

Following sporulation (described above), the oocyst preparation may be subjected to additional purification procedures (e.g., density filtration, flotation and the like), followed by sanitization. Alternatively, a sanitizing step may be used prior to or concurrently with the sporulation step. Generally, however, it is advantageous to sanitize the oocysts near the end of the purification process as steps after sanitization will be carried out using sterile procedures and reagents.

By "sanitizing" or "sanitization" or "sanitized" it is intended that there is a reduction in the contaminating microbial load (i.e., viable contaminating microorganisms, as defined above) in the oocyst preparation. It is not necessary that the oocyst preparation contain absolutely no microbial contamination, as long as the final preparation is suitable for its intended use (e.g., as a vaccine). In the case of vaccines intended for in ovo administration to birds, the preparation will generally be essentially free of detectable microbial contamination (i.e., no significant levels of contaminating microorganisms are detected). In other embodiments, there is at least about a 50%, 60%, 75%, 85%, 90%, 95%, 99% or more reduction in detectable contaminating microorganisms as compared with the level in the absence of sanitization.

Methods of detecting microorganisms are known in the art and depend on the class of microorganism being detected.

Accordingly, the present invention provides a method of sanitizing oocysts, comprising the step of providing a composition containing oocysts, and sanitizing the oocysts in a sanitizing medium of the invention (as described above) for a time and under conditions sufficient to achieve the desired level of sanitization of the composition. In embodiments of the invention, the sanitizing process results in a preparation with a level of microbial contamination that is suitable for administration to an animal subject (e.g., in in ovo vaccination methods). The sanitizing procedure may be carried out for any suitable length of time, typically for about one hour to about 12, 24 or 48 hours.

In other particular embodiments, the sporulation and sanitization processes are carried out concurrently.

The temperature of the sanitizing process is not critical and may generally be carried out at a temperature from about 4° C. to about 40° C. Preferably, the oocysts are not subjected to freezing or prolonged exposure to high temperatures (e.g., exposure to 40° C. would typically be for less than a few hours or even less than 1 hour). In one exemplary embodiment, sanitization is carried out for about 24 to 72 hours at about 30° C.

The ratio of the oocyst preparation to sanitization medium is not critical as long as it is sufficient to reduce microbial growth to the desired level. Exemplary ratios of feces to collection medium are about 1:0.25, about 1:0.5, about 1:1, about 1:2, about 1:3, about 1:4, about 1:5, or about 1:10 (v/v).

Following sanitization, steps may be taken to remove the peroxygen compound, e.g., using catalytic decomposition (e.g., an enzymatic process or chemical treatment such as with manganese dioxide), dilution, dialysis and/or filtration. For example, in the case of hydrogen peroxide, catalase may be used to reduce or remove residual hydrogen peroxide.

As another optional step, the oocyst preparation may be contacted with (e.g., sprayed, rinsed or mixed with) a composition that decreases aggregation among the oocysts, such as an solution (e.g., an aqueous solution) containing protein, peptides, protein hydrolysate and/or amino acids. Illustrative compounds include but are not limited to soy protein, soy hydrolysate, casein, casein hydrolysate, lysozyme, albumen, bovine serum albumen, milk proteins, amino acids (e.g., arginine, phenylalanine and/or aspartic acid), fetal calf serum, chicken serum, whole milk, and the like. In one particular embodiment, the anti-aggregation solution comprises a positively charged amino acid, a negatively charged amino acid and a neutral amino acid.

Typically, the concentration of each component in the solution will be about 0.01 M to 10M, about 0.05M to 5M or about 0.05M to about 2M.

The pH of the solution may be chosen in accordance with the particular components used in the medium, and may be in the acidic, neutral or alkaline range. In particular embodiments, the pH of the anti-aggregation solution is in the neutral range. For example, the solution may be buffered with phosphate buffer saline (pH 7) or Hanks Balanced Salt Solution (pH 7).

Other compounds may be used as well to reduce aggregation, such as an anti-foaming agent (e.g., antifoam A).

The oocysts may be contacted with the anti-aggregation medium at any point in the purification process in which it is desirable to reduce aggregation among the oocysts. It may be advantageously used after the sanitization process. In particular embodiments, in the absence of a sanitization step (e.g., in some post-hatch vaccine products), this process may be used to reduce aggregation in the final product. Alternatively or additionally, the anti-aggregation solution may be added to the final formulation to reduce oocyst aggregation therein.

Flotation Medium for Oocyst Separation.

One conventional technique used for purifying oocysts from fecal material and other unwanted debris relies on density flotation of the oocysts through a high-density medium such as a saturated sodium chloride or sucrose solution and recovery of the fraction containing the oocysts. Flotation methods may be used prior to and/or after sporulation. Ionic solutions such as sodium chloride may damage the oocysts upon prolonged exposure (Ryley and Ryley, (1978) *Parasitology* 77:33-39). Non-ionic solutions, such as a concentrated sucrose solution, have also been used in flotation procedures. One drawback of any solid reagent, such as sodium chloride or sucrose, is that they must be dissolved in an aqueous solution prior to use.

In U.S. Pat. Nos. 4,544,548 and 4,863,731 to Davis et al., a method for the control of coccidiosis in poultry is demonstrated. These patents describe the use of a salt flotation process, i.e., flotation in a dense salt solution using centrifugation and followed by dilution and recovery of oocysts in a second centrifugation step.

Ryley, et al. ((1976) *Parisitology* 73(3):311-326) describes a method to separate oocysts from feces using sucrose, sodium chloride, and zinc sulfate flotation.

Vetterling, J. M. ((1969) *J. Parasitology* 55(2):412-417) describes continuous-flow centrifugation techniques: flotation in high density sucrose solution, dilution with water, and recovery of oocysts by additional centrifugation.

Marquardt, W. C. ((1961) *J. Parasitology* 47:248-250) describes the separation of nematode eggs from fecal debris by gradient centrifugation. Patnaik, B. ((1966) *Indian Vet. J.* 43:414-422) discloses a technique of obtaining coccidia oocysts in pure state from chicken feces by a modification of Marquardt's method.

Sharma and Reid ((1963) *J. Parasitology* 49:159-160) discloses a cleaning method for coccidial oocysts using density-gradient sedimentation.

International patent publication WO 00/50072 (Pfizer, Inc.) describes the use of a sodium sulfate flotation process.

Dulski et al., (1988) *Avian Diseases* 32:235, describes the use of colloidal silica suspensions (Percoll™) for density flotation of oocysts.

The present invention provides a flotation medium for purifying oocysts from unwanted matter comprising a high density, non-ionic liquid and a polycation molecule or particle. The high-density, non-ionic liquid may be any aqueous liquid that has a density of about 1.08, 1.1, 1.12, 1.14, 1.16, 1.18, or 1.2 g/ml. Typically, the density will not be higher as most commercial centrifuge equipment is not intended for use with higher density solutions. In embodiments of the invention, the high-density, non-ionic solution is glycerol, sorbitol, sucrose, high fructose corn syrup, hydroxymethylcellulose, or a combination thereof.

The present inventors have discovered that polycationic molecules or particles may be used to improve the debris removal characteristics of non-ionic flotation media. Any suitable polycation known in the art may be included in the flotation medium. Illustrative polycations include arginine, histidine, lysine, diethylaminoethyl-cellulose (DEAE-cellulose), and polyvalent metal ions (e.g., iron or aluminum salts such as aluminum sulfate and ferric chloride). The concentration of the polycation is not critical, but is preferably sufficiently high to promote flocculation of debris, but insufficient to unduly damage the oocysts. Exemplary concentrations of the polycation in the medium are from about 0.01 M, 0.05 M or 0.1M to about 0.5 M, 1 M, 3 M or higher.

The flotation medium may contain other ingredients such as buffers or antimicrobial agents. In particular embodiments, the flotation medium includes a non-ionic detergent (e.g., Tween-20) and/or an anti-foaming agent (antifoam A) to decrease the likelihood of the oocysts forming clumps.

The present invention also encompasses methods of purifying oocysts using a density flotation procedure. In particular embodiments, the method comprises: suspending a preparation containing oocysts in a composition comprising a high density, non-ionic liquid and a polycation to form a suspension under conditions sufficient to result in flotation of the oocysts, and recovering the oocysts from the suspension. Generally, the material containing the oocysts is admixed with the flotation solution, and the solution is allowed to separate, with the oocysts remaining in the supernatant fraction and the fecal debris forming a pellet. Centrifugation may be used to facilitate or improve the separation.

The inventors have further found that the flotation procedure may be enhanced by adding oil to a flotation medium comprising a high-density nonionic flotation medium (with or without a polycation). The oil may be any suitable oil known in the art, including but not limited to, corn oil, safflower oil, peanut oil, canola oil, soybean oil, and the like. The addition of oil may improve the removal of debris and may achieve improved levels of separation in the absence of high-speed centrifugation and may even eliminate the need for centrifugation at all.

There are no particular limits to the concentration of oil in the flotation process. Oil is generally used in the flotation medium at a concentration of about 1% to about 10% or about 3% to about 7% of the total volume of the flotation solution.

Alternatively, an oil flotation step may be performed before or after flotation in the high-density non-ionic solution containing polycation, described above.

Following the flotation step(s), the recovered fraction containing the oocysts may be further processed by any suitable method known in the art. For example, the fraction may be subjected to further purification procedures, and/or sporulation and/or sanitization as known in the art or as disclosed herein.

The flotation medium may be removed from the oocysts by any method known in the art, including centrifugation/wash steps, dialysis and filtration (e.g., tangential flow filtration).
Production Diet.

With particular respect to the production of oocysts in birds, the inventors have found that the diet the birds are fed at or around the time the oocysts are shed into the feces may impact the process of separating the oocysts from the fecal matter. According to traditional methods, poultry are generally fed a mash or crumble complete diet throughout the period in which oocysts (e.g., *Eimeria* oocysts) are shed into the feces. After fecal material containing oocysts has been collected, the initial purification steps rely on bulk techniques such as sieving and/or filtration. Normal poultry diet contains very fine particles, which may be difficult to separate from the oocysts. As far as the inventors are aware, the investigations described herein are the first to address and appreciate the effect of diet on the process of purifying oocysts from animal feces.

The present inventors have found that separation of oocysts from fecal material may be enhanced (i.e., improved) by maintaining the infected bird on a large particle diet, i.e., a diet having a large mean diameter size. The diet typically contains a substantial proportion of ingredients that are unground (i.e., whole grain) or only partially ground or that are extruded or extracted. Exemplary ingredients include cracked corn, extruded soybeans, whole oats, and combinations thereof. In some embodiments, the grains have been sieved to remove fines. In particular embodiments of the invention, the large particle diet contains less than about 40% (w/w), less than about 30% (w/w), less than about 20% (w/w), less than about 10% (w/w), less than about 5% (w/w), or even less, ground feed or meal (e.g., ground corn, soybean, fish or bone meal, and the like). In other embodiments, the large particle diet contains essentially no ground meal components. Those skilled in the art will appreciate that vitamins, minerals, amino acids, and other micronutrients will typically be added to the meal in a granular premix formulation.

Illustrative poultry diets contain at least about 30%, 40%, 50%, 60%, 70%, 80%, 90%, 95% or higher (w/w) extruded soybeans, cracked corn, whole oats and/or other unground or only partially ground, extruded or extracted feed components as known in the art, as well as any vitamins, minerals, amino acids and salts to maintain the nutritional health of the bird. In one particular embodiment, chickens are fed a diet consisting essentially of 45-55% (w/w) extruded soybeans, 35-40% (w/w) cracked corn, and 5-15% (w/w) whole oats, as well as vitamins, minerals, amino acids and salts to maintain the nutritional health of the bird.

In general, at least about 30%, 35%, 40%, 50%, 60%, 70% (w/w) or more of the feces produced by a bird maintained on the large particle diet during the collection period are retained by a 0.5 mm screen. Alternatively, at least about 40%, 50%, 60%, 70%, 80%, 90%, 95% (w/w) or more of the feces are retained by a 0.075 millimeter screen.

The bird may be fed the large particle diet from hatch. Alternatively, the bird is started on normal poultry diet and then is switched to the large particle diet at some point at or prior to the collection period, e.g., at least about seven days, five days, three days, two days, one day, or twelve hours prior to collection or, alternatively, at the time collection commences. The birds are generally maintained on the large particle diet throughout the collection period. The birds may be fed the large particle diet for less than the entire collection period as long as some improvement or advantage in purification is observed.

The feces containing the shed oocysts are typically collected during the peak output period for each species, typically starting three, four or five days after infection and continuing collection for about two to four days thereafter, depending on the species. In embodiments of the invention, the collection period takes place at some time from about 3-9 or from about 4-8 days post-infection.

The large particle production diet of the invention may result in easier debris removal, improved yields of the oocysts, and/or reduced production costs.

The Examples, which follow, are set forth to illustrate the present invention, and are not to be construed as limiting thereof.

EXAMPLE 1

Oocyst Production Diet

This Example describes an oocyst production diet consisting of combinations of large particles with typical dietary supplements (vitamins, minerals, trace nutrients). The large particle components may consist of cracked corn, extruded soybeans, and/or whole grains such as oats. This diet was developed to improve oocyst output and yield while maintaining the proper nutrition of the bird and facilitating oocyst isolation. The regimen may include use of a normal poultry diet until just prior to the beginning of the collection period, when the birds are switched to a large particle diet for the duration of the oocyst output period. The advantages of this diet are that it is easier to remove debris by sieving and filtration, it improves oocyst yields, and it reduces production costs.

Sieving processes are routinely used in oocyst purification. The sieving process can be facilitated by development of a diet formulation using a high percentage of large particles which are retained on the sieves. Four experimental diets were tested for oocyst output using normal poultry diet as a control. Cobb×Cobb broilers were used for production of *E. maxima* oocysts. Five replicates of each treatment were used. In this Example, large particle diets were fed throughout the experiment, without supplementation with normal poultry diet. Fecal samples were collected during the peak output period (days 5 to 8 post gavage) and brought to a standard volume, mixed well and subsampled for oocyst enumeration and debris determination. Each sample was then processed through a 35 mesh approximately 0.5 mm) sieve, brought to a standard volume, mixed well and subsampled for oocyst enumeration and debris determination. Results are presented in the Table 1.

TABLE 1

| Treatment | Description | Average Total Solids (mL) Presieving | Average Oocyst Recovery (%) <35 mesh | Average Total Solids (mL) <35 mesh | Percent Solids Removed using 35 mesh sieve |
|---|---|---|---|---|---|
| Standard | Standard Broiler Diet | 1225 | 85 | 1166 | 5 |
| Diet 2 | Cracked corn, extruded soybeans, fishmeal | 913 | 96 | 668 | 27 |
| Diet 3 | Cracked corn, extruded soybeans, finely ground corn | 935 | 91 | 554 | 41 |
| Diet 4 | Cracked corn, extruded soybeans, finely ground corn, fishmeal | 1040 | 99 | 574 | 45 |
| Diet 5 | Cracked corn, extruded soybeans, whole oats | 1118 | 98 | 604 | 46 |

The results of these experiments indicate that initial debris levels were highest using normal poultry diet. Diets 2-5 (large particle diets) yielded starting debris levels which were lower than normal poultry diet, and which were similar for all experimental diets. Oocyst recovery after the 35 mesh sieve was higher for the large particle diets (91 to 99%) than for normal poultry diet (85%). Finally, up to 46% of the debris was removed by the 35 mesh sieve when the large particle diets were used, compared to only 5% of the debris being removed by the 35 mesh sieve when normal poultry diet was used.

EXAMPLE 2

Pilot Scale Use of Oocyst Production Diet

*E. maxima* oocysts were produced using broilers in cages (540 birds total). Primary feed was Diet 5 (large particle diet) described in Example 1; supplemental trays of standard broiler diet were also provided through D5. Oocyst inoculum was administered via oral gavage to the crop (20,000 sporulated oocysts per bird). Feces were collected into 10% citric acid, 0.25% propionic acid solution (2 liters per pan) from day 5 to day 8 post inoculation. Upon harvest, the following steps were performed for each run:

Pooled; measured the volume of the pooled sample; sub-sampled.

Sieved through stacked 18 mesh (1 mm) and 60 mesh (~0.25 mm) screens using a vibratory sieve.

Sieved through a 200 mesh (0.075 mm) screen using a vibratory sieve.

Oocysts were enumerated using the McMasters method

Debris levels were determined by centrifuging a small sample and measuring the ratio of the volume of pelleted solids to the total volume centrifuged.

The results are summarized in Table 2 below:

TABLE 2

| Run | Oocyst Recovery through 18 and 60 mesh Step yield (%) | Oocyst Recovery through 200 mesh Step yield (%) | Total Solids start (L) | Total Solids <60 mesh (L) | Total Solids <200 mesh (L) | Solids reduction from sieving (%) |
|---|---|---|---|---|---|---|
| 1 | 83 | 97 | 73 | 37 | 20 | 72.6 |
| 2 | 88 | 95 | 70 | 30 | 21 | 70.0 |
| 3 | 93 | 75 | 75 | 35 | 20 | 73.3 |
| 4 | 89 | 85 | 125 | 51 | 30 | 76.0 |
| 5 | 81 | 78 | 91 | 42 | 22 | 75.8 |
| 6 | 73 | 98 | 107 | 46 | 39 | 63.6 |
| 7 | 80 | 73 | 118 | 65 | 33 | 72.0 |
| 8 | 114 | 84 | 107 | 50 | 27 | 74.8 |
| Average | 88 | 86 | 96 | 45 | 27 | 72 |
| Standard deviation | 12.3 | 10.0 | 21.5 | 11.1 | 7.0 | 4.1 |
| Coefficient of Variation (%) | 14.1 | 11.7 | 22.5 | 24.9 | 26.5 | 5.6 |

The results demonstrate oocyst recoveries with Diet 5 averaging 86 to 88% with CVs<15%. An average of 72% of the starting solids were removed during the sieving step.

EXAMPLE 3

Use of Peroxygen and Organic Acid Based Medium for Collection and Sporulation of Oocysts This example, as well as the following two Examples, describe a collection/sporulation/sanitization medium which protects oocysts from drying out, reduces the bioburden from the start of the collection period, yields high sporulation rates, is easier to dispose of than potassium dichromate, and is a more gentle sanitization reagent than hypochlorite.

A medium consisting of 0.75% hydrogen peroxide, 10% citric acid, 0.25% propionic acid, and 0.1% Antifoam A was developed which can serve as a medium for collection and sporulation of oocysts. The aqueous medium protects the oocysts from drying out, acts as an anti-microbial medium to kill viruses and prevent the buildup of bacterial or mold during the collection process, and promotes sporulation during the collection process. Antifoam A is added to prevent excessive foaming of the fecal suspension, and serves to reduce oocyst clumping. The antifoam A, however, is optional in the medium. Other peroxygen compounds such as sodium perborate (the monohydrate or tetrahydrate form) could be used either in place of or in combination with hydrogen peroxide.

Oocysts of various *Eimeria* species were produced in chickens and collected into the medium during the peak output period for each species. Approximately 2 to 3 liters of collection medium were used to collect the feces from 8 to 10 birds. At the end of the collection period, oocysts were purified using sieving and density flotation techniques. Oocysts were then placed in fresh sporulation medium, stirred and aerated for 72 h. Sporulation rates were determined using standard microscopic techniques immediately after collection and again after processing through sieving, flotation, and 3-day sporulation treatment. Results are shown in Table 3:

TABLE 3

| *Eimeria* species | Sporulation (%) (prior to processing) | Sporulation (%) (after processing) |
|---|---|---|
| E. maxima | 82.3 | 94.3 |
| E. mitis | 92.7 | 92.8 |
| E. tenella | 78.3 | 97.6 |
| E. acervulina | 89.7 | 91.7 |

When oocysts were collected in the new medium, the majority of the sporulation process was observed to have occurred prior to processing, and high final sporulation rates were observed for all *Eimeria* strains tested. These results suggest that the proposed collection and sporulation medium provides an effective method for achieving high levels of sporulation during the oocyst collection period, even before performing the standard 48- to 72-hour sporulation process.

EXAMPLE 4

Demonstration of Fungistatic and Fungicidal Properties of Peroxygen and Organic Acid Based Sanitization Medium An experiment was conducted to assess the fungistatic or fungicidal properties of the reagents used in the collection and sporulation medium described in Example 3. Initial sterility tests were performed using trypticase soy broth (TSB). A fungal stock was created by suspending fungal scrapings from a *Scopulariopsis brumptii* stock culture into 25 mL PBS and filtering this material through a coarse Swinney filter (~100 μm). Two hundred Ml of this fungal stock was inoculated into three TSB flasks for treatments (Trt) 2-11.

Treatments evaluated various of the components of the collection/sporulation/sanitization medium described in Example 3, either alone or in combination. Sodium propionate was also tested in addition to propionic acid. Treatments were evaluated at room temperature for 28 days; then, on day 28 of incubation, one mL of each replicate flask for all treatments was plated onto a malt extract agar (MEA) plate with chloramphenicol (50 μg/mL) and penicillin-G (100 U/mL) and incubated at room temperature for 14 days. The reagent was considered fungistatic if no growth was observed in the 28-day incubation of the TSB flasks (−) and growth was observed when the medium in the flask was transferred to the MEA plates(+). The reagent was considered fungicidal if no growth was observed in the TSB flasks(−) or upon transfer to MEA plates(−). Results are presented in Table 4.

TABLE 4

| Trt | Description | Growth in TSB Flasks (Day 28) | Growth on MEA plates (Day 14) |
|---|---|---|---|
| 1 | Media control | − | − |
| 2 | Fungus control | + | + |
| 3 | 0.75% hydrogen peroxide in media | − | − |
| 4 | 0.25% propionic acid in media | − | + |
| 5 | 10% citric acid in media | − | − |
| 6 | 0.75% hydrogen peroxide, 0.25% propionic acid in media | − | − |
| 7 | 0.75% hydrogen peroxide, 10% citric acid in media | − | − |
| 8 | 10% citric acid, 0.25% propionic acid in media | − | − |
| 9 | 0.75% hydrogen peroxide, 10% citric acid, 0.25% propionic acid in media | − | − |
| 10 | 0.25% sodium propionate in media | + | + |
| 11 | 0.5% sodium propionate in media | + | + |

The media controls remained negative for fungal growth in this experiment and the fungal controls were positive, as expected. In both the flask and plate tests, sodium propionate (0.25% or 0.50%) did not inhibit fungal growth. The propionic acid treatment (0.25%) in media (Treatment 4) was fungistatic; it inhibited fungal growth in the flask, but not on the MEA plates. All other treatments (excluding the controls) were apparently fungicidal, with no observed fungal growth in the flasks and no growth on the plates. These results indicate the potent fungistatic and fungicidal properties of the reagents used in the proposed formulation (Treatment 9).

EXAMPLE 5

Use of Peroxygen and Organic Acid Based Sanitization Medium in Oocyst Production An experiment was performed to investigate the utility of the sporulation medium described in Example 3 as a sanitization reagent. *E. maxima* oocysts were produced in broilers and purified using a density flotation technique. Oocysts were sporulated for 72 h using 10% citric acid, 0.25% propionic acid, 0.75% hydrogen peroxide, and 1 mL/L Antifoam A. After sporulation, the oocysts were centrifuged and resuspended in sterile-filtered sporulation medium (10% citric acid, 0.25% propionic acid, 0.75% hydrogen peroxide, 1 mL/L Antifoam A) and incubated overnight at room temperature with stirring. After sanitization, buffer exchange was accomplished via diafiltration using 200 mM potassium phosphate, pH 7, followed by PBS without preservatives. The bulk sample was stored in glass bottles approximately one-third full at 4° C. Subsamples of the final product were sent to a commercial testing laboratory for purity tests according to U.S. Department of Agriculture (USDA) guidelines. The results of 9CFR sterility tests after sanitization using peroxide-based medium are shown in Table 5.

TABLE 5

| USDA Test Number | Description | Test Period (Days) | Results |
| --- | --- | --- | --- |
| 9CFR 113.27 | Detection of extraneous viable bacteria and fungi in live vaccine | 28 | Negative |
| 9CFR 113.28 | Detection of mycoplasma | 28 | Negative |
| 9CFR 113.30 | Detection of salmonella | 4 | Negative |
| 9CFR 113.31 | Detection of avian lymphoid leukosis | 30 | Negative |
| 9CFR 113.34 | Detection of hemagglutinating virus | 7 | Negative |

All test results indicate that the sterile-filtered sporulation medium may be used as an effective alternative to sodium hypochlorite for sanitization of oocysts.

EXAMPLE 6

Sanitization of Oocysts Using a Peroxygen and Organic Acid Based Medium

Two experimental batches of *E. maxima* oocysts were prepared (Run A and Run B). Each batch was purified using sieving and flotation procedures. Each batch was then split and two methods of sanitization were tested (sodium hypochlorite and hydrogen peroxide with citric acid and propionic acid). Samples from each test were subjected to several purity tests including 9CFR tests and two PCR methods for virus detection. The results are shown in Table 6:

TABLE 6

| Purity test | Description | Run A Hypochlorite | Run A Hydrogen Peroxide With citric acid and propionic acid | Run B Hypochlorite | Run B Hydrogen Peroxide With citric acid and propionic acid |
|---|---|---|---|---|---|
| 9CFR 113.27 | Detection of extraneous viable bacteria and fungi in live vaccine | Negative | Negative | Negative | Negative |
| 9CFR 113.28 | Detection of mycoplasma | Negative | Negative | Negative | Negative |
| 9CFR 113.30 | Detection of salmonella | Negative | Negative | Negative | Negative |
| 9CFR 113.31 | Detection of avian lymphoid leucosis | Negative | Negative | Negative | Negative |
| 9CFR 113.34 | Detection of hemagglutinating virus | Negative | Negative | Negative | Negative |
| 9CFR 113.55 | Extraneous agents in master seed | Negative | Negative | Negative | Negative |
| | Chicken Infectious Anemia Virus by PCR | Negative | Negative | Negative | Negative |
| | Reticuloendothelial Virus by PCR | Negative | Negative | Negative | Negative |

The results from the purity tests indicate that all sanitized materials are free of contaminating microorganisms, and that the hydrogen peroxide sanitization solution was as effective as hypochlorite.

EXAMPLE 7

Flotation of *E. maxima* Oocysts in Glycerol-Based Solutions

The next two Examples describe flotation media for oocyst separation using molecules or particles with multiple positive charges (for example, 0.1 M arginine). These molecules may be used to improve the debris-removal characteristics of non-ionic flotation media (for example, sucrose, glycerol, high fructose corn syrup), and additives such as non-ionic detergents (for example, Tween-20) or antifoaming agents (for example, Antifoam A) may be used to reduce clumping of oocysts and thereby optimize the flotation process. The advantages of these flotation media include improved debris removal, non-ionic solution may be less damaging to oocysts than salt solutions, and positively charged species act as a flocculation aid to bind small debris particles together and provide more efficient pelleting of debris particles during centrifugation.

Chicken feces containing *E. maxima* oocysts were processed using five different flotation media. The starting material was composed of pooled materials from approximately 150 birds. The pooled sample was sieved using a mechanical sieving device followed by a fine mesh screen. The sieved sample was centrifuged in 750 mL aliquots to pellet the oocysts. The supernatants were decanted and pellets were resuspended using: 1) 20% sodium sulfate, 2) 60% glycerol, 3) 60% glycerol +0.1M arginine, 4) 60% glycerol +10 g/L DEAE-cellulose, or 5) 60% glycerol +0.1M arginine +10 g/L DEAE-cellulose. Each medium was used at 5× the pellet volume to resuspend three pellets representing approximately 2250 mL of sieved sample. The 20% sodium sulfate medium was centrifuged at 1000 rpm for 10 minutes at 10° C.; all other treatments were centrifuged at 3000 rpm for 10 minutes at 10° C. Results for the flotation treatments are summarized in the Table 7.

TABLE 7

| Treatment | Step | mL solids per bird | Total Oocysts per bird (×10⁷) | Oocyst Yield (%) | Oocysts per mL solids (×10⁶) | Fold Improvement |
|---|---|---|---|---|---|---|
| 20% sodium sulfate | Resuspended solids | 77.51 | 2.20 | 100.0 | 0.28 | |
| | Post flotation | 28.07 | 2.12 | 96.2 | 0.75 | 2.7 |
| 60% glycerol | Resuspended solids | 68.90 | 2.04 | 100.0 | 0.30 | |
| | Post flotation | 14.04 | 1.78 | 87.1 | 1.27 | 4.2 |
| 60% glycerol + arginine | Resuspended solids | 86.12 | 1.71 | 100.0 | 0.20 | |
| | Post flotation | 2.81 | 1.62 | 94.8 | 5.76 | 28.8 |
| 60% glycerol + DEAE cellulose | Resuspended solids | 74.64 | 2.24 | 100.0 | 0.30 | |
| | Post flotation | 5.61 | 1.76 | 78.4 | 3.13 | 10.4 |
| 60% glycerol + arginine + DEAE-cellulose | Resuspended solids | 71.77 | 1.63 | 100.0 | 0.23 | |
| | Post flotation | 2.81 | 1.69 | 103.6 | 6.02 | 26.2 |

In this experiment, all of the flotation media yielded fairly good oocyst recovery, ranging from 78.4% to 103.6%. All of the glycerol-based media were more efficient for debris removal than the sodium sulfate medium. Percent solids reduction for the sodium sulfate medium was 63.8%, while the glycerol-based media ranged from 79.6% to 96.7%. The addition of a positively charged molecule (arginine) or particle (DEAE-cellulose) improved removal of debris when compared with glycerol alone. The standard sodium sulfate flotation method yielded a 2.7-fold increase in oocysts per mL solids, while a method using flotation in 60% glycerol +0.1M arginine yielded a 28.8-fold increase in oocysts per mL solids.

EXAMPLE 8

Flotation of *E. maxima* Oocysts in Glycerol- and Sucrose-Based Media

Alternative flotation media were tested using chicken feces containing *E. maxima* oocysts produced in broilers. A 36-hour feed withdrawal period was used prior to fecal collection. While glycerol-arginine media are highly effective in terms of oocyst recovery and debris removal, the expense of glycerol on a larger scale may be prohibitive. To utilize the charge interactions between arginine and the fecal debris, the effects of a non-ionic density enhancer were investigated. In this experiment, various formulations based on either glycerol or sucrose as non-ionic compounds were compared.

Prior to flotation, feces were processed though coarse and fine mesh sieves to remove large debris particles. The sieved sample was centrifuged in 700 mL aliquots to pellet the oocysts. The supernatants were decanted and pellets were resuspended using the test formulations indicated below. Approximately equivalent portions were used for each test medium. Each medium was used at 5× the pellet volume to resuspend three pellets representing approximately 2100 mL of sieved sample. Pooled resuspended pellets were passed through a coarse screen to ensure resuspension of clumps. Clumps were rinsed through the screen with a small amount of the appropriate flotation medium.

Flotation Media:

A. 60% glycerol, 0.1 M arginine

B. 60% glycerol, 0.1 M arginine, 0.2% Tween-20, 1 mL/L Antifoam A

C. 1.5M Sucrose, 0.1 M arginine

D. 1.5M Sucrose, 0.1 M arginine, 0.2% Tween-20, 1 mL/L Antifoam A

E. 1.5M Sucrose, 0.1 M arginine, 0.2% Tween-20, 1 mL/L Antifoam A, 0.1% xanthan gum Results for the flotation treatments are summarized in the Table 8.

TABLE 8

| Flotation Medium | Sample | mL solids per bird | Total oocysts per bird ×10⁷ | Yield % | Oocysts Per mL Solids ×10⁶ | Fold Improvement |
|---|---|---|---|---|---|---|
| A | Resuspended solids | 35.02 | 1.26 | 100.00 | 0.36 | |
| | Post float | 1.86 | 1.25 | 99.66 | 6.72 | 18.7 |
| B | Resuspended solids | 38.92 | 1.48 | 100.00 | 0.38 | |
| | Post float | 1.74 | 1.29 | 87.54 | 7.45 | 19.6 |
| C | Resuspended solids | 40.03 | 1.63 | 100.00 | 0.41 | |
| | Post float | 1.98 | 1.46 | 90.01 | 7.39 | 18.2 |
| D | Resuspended solids | 36.14 | 1.66 | 100.00 | 0.46 | |
| | Post float | 1.74 | 1.19 | 71.85 | 6.85 | 14.9 |
| E | Resuspended solids | 31.32 | 1.48 | 100.00 | 0.47 | |
| | Post float | 2.48 | 1.08 | 72.87 | 4.36 | 9.2 |

Glycerol-arginine either with or without additives yielded good oocyst recovery and improvement in oocyst purification (approximately 19-fold improvement in oocyst per ml solids over previous step). While the sucrose-arginine medium alone yielded good oocyst recovery (90%) and good debris removal (18-fold improvement over previous step), the addition of 0.2% Tween-20 and 1 mL/L Antifoam yielded a slight drop in both measures of performance. Enhancing the viscosity of the sucrose-arginine-Tween-20-Antifoam A medium with xanthan gum had essentially no effect on oocyst recovery but adversely affected debris removal.

Therefore, positively charged molecules (such as arginine) or positively charged particles (such as DEAE-cellulose) can enhance debris removal when used with non-ionic flotation media. Non-ionic flotation media include formulations such as aqueous glycerol solution, aqueous sucrose solution, aqueous high fructose corn syrup solution, or other similar solutions. It is possible that the positively charged moieties act as flocculation aids, binding together negatively charged debris particles, and thus providing for more efficient pelleting of the debris during centrifugation. The recovery of oocysts and the enhanced debris-removal effects may be optimized using other additives such as Tween-20 or Antifoam A.

EXAMPLE 9

Oil-enhanced Oocyst Flotation Technique

This Example describes experiments designed to investigate the effects of oil in the oocyst flotation process. The oil-assisted process may improve separation of oocysts from solids and allow the process to be performed at 1×g thereby avoiding the use of expensive centrifugation equipment at higher g forces.

Experimentation was conducted to determine if a gentle continuous flotation method could be used for separation of oocysts from fecal debris. Separation may be accomplished by capitalizing on differences in density, using a continuous stirring process in which the oocysts slowly rise to the top of the medium where they can be skimmed off and recovered from fecal debris.

In the initial trials a partially purified (sieved and sporulated) batch of E. maxima oocysts was used. High-Fructose-Corn-Syrup (HFCS), CornSweet 55 (ADM, Illinois) and sodium chloride salt were used as density increasing agents in several combinations. The material was placed in a 1 L polypropylene beaker and slowly mixed with HFCS and NaCl using an IKA Labortechnik batch mixer. Samples were taken from the top of the suspension, and then from near the bottom of the container. Additional HFCS was added after sampling, the material was slowly mixed further, then a second set of samples taken.

The top layer samples (F-1, F-2) were collected using a 25 mL pipette or plastic spoon into a 50 mL polypropylene tube (25 ml per sample). The bottom samples (S-1, S-2) were drawn with 25 mL pipette into 50 mL polypropylene tube (25 mL per sample). All samples were diluted 10 times with distilled water and transferred and into 250 mL bottles. From every bottle two subsamples were taken and diluted 10 times with 1× PBS buffer. Oocysts were counted in these diluted subsamples using McMaster's method. The results of this experiment are shown in Table 9.

TABLE 9

| Fecal suspension (mL) | Water (mL) | HFCS (g) | NaCl (g) | Counts - Top Layer (# oocysts per chamber) | Counts - Bottom Layer (# oocysts per chamber) |
|---|---|---|---|---|---|
| 750 | 250 | 100 +80 | 20 | 82, 90 60, 68 | 52, 47 41, 45 |
| 750 | 250 | 150 +50 | 45 | 52, 58 21, 30 | 23, 20 38, 22 |

TABLE 9-continued

| Fecal suspension (mL) | Water (mL) | HFCS (g) | NaCl (g) | Counts - Top Layer (# oocysts per chamber) | Counts - Bottom Layer (# oocysts per chamber) |
|---|---|---|---|---|---|
| 500 | 500 | 150 +50 | 45 | 35, 40 36, 38 | 18, 15 21, 14 |

The data indicate that although there was clearly enrichment of oocysts in the upper layers of the suspension, the oocysts did not float efficiently and form a distinct top layer in any of the tested conditions (i.e., in the absence of centrifugation). The ratio of HFCS to NaCl or further dilution of fecal suspension did not influence flotation in this study. It was found to be difficult to sample the top layer of the tested suspensions.

After these experiments, it appeared that either a significant dilution of the material or an introduction of a flotation-enhancing-agent would be useful to facilitate oocyst movement through the fecal material. An experiment was performed to determine the utility of vegetable oil as a flotation-enhancing agent.

In a 1 L polypropylene beaker, 500 mL of the original oocyst suspension and 500 mL of water containing 160 g of High Fructose Corn Syrup+40 g of NaCl+50 mL of safflower oil were mixed using an IKA batch mixer. The mixer was operated in the following sequence: fast-slow-stop-slow-stop. The top layer (50 mL) was spooned into the 250 mL bottle containing 200 mL of water. The bottle's contents were mixed thoroughly. Three distinct layers formed within minutes. Two subsamples from the each layer were taken and oocysts were counted using a McMaster chamber. The results are shown in Table 10.

TABLE 10

| Layer | Oocyst count - subsample 1 | Oocyst count - subsample 2 |
|---|---|---|
| Top oil layer | 2 | 4 |
| The thin layer under the oil layer | 110 | 121 |
| The bulk bottom layer (~93%) | 0 | 0 |

These results indicate that the oil facilitated the oocyst flotation process. One advantage of this oil-assisted flotation process is that the oocyst layer formed quickly without requiring centrifugation, that is, at 1×g. Typically, oocyst flotation processes use centrifugation at forces of 2000×g or even higher to achieve separation of the oocyst layer from the debris.

The foregoing examples are illustrative of the present invention, and are not to be construed as limiting thereof. The invention is described by the following claims, with equivalents of the claims to be included therein.

What is claimed is:

1. A method of sporulating viable *Eimeria* oocysts: the method comprising: a. providing non-sporulated, viable *Eimeria* oocysts; and b. contacting the non-sporulated, viable *Eimeria* oocysts with a composition comprising a peroxygen compound and a combination of citric and propionic acids to effect sporulation, said composition having an acidic pH of less than pH 4 wherein said method does not include the use of potassium dichromate.

2. The method of claim 1, wherein the *Eimeria* is selected from the group consisting of *E. maxima, E. mitis, E. tenella, E. acervuline, E. brunetti E. necatrix, E. praecox, E. mivati* and a combination thereof.

3. The method of claim 1, wherein the pH of the composition is from about pH 1.0 to about pH 3.0.

4. The method of claim 1, wherein the concentration of the peroxygen compound in the composition is from about 0.1% to about 10% (v/v) or (w/v).

5. The method of claim 1, wherein the peroxygen compound is selected from the group consisting of hydrogen peroxide, sodium perborate, sodium percarbonate, magnesium peroxide, calcium peroxide, zinc peroxide, urea peroxide and a combination thereof.

6. The method of claim 5, wherein the peroxygen compound is hydrogen peroxide.

7. The method of claim 6, wherein the concentration of hydrogen peroxide in the composition is from about 0.1% (v/v) to about 3% (v/v).

8. The method of claim 7, wherein the concentration of hydrogen peroxide in the composition is from 0.25% (v/v) to about 1% (v/v).

9. The method of claim 1, wherein the concentration of organic acids in the composition is from about 1.0% to about 15% (v/v) or (w/v).

10. The method of claim 1, wherein the *Eimeria* comprises a species of *Eimeria* that infects birds.

11. The method of claim 10, wherein the *Eimeria* comprises a species of *Eimeria* that infects turkeys.

12. The method of claim 1, wherein the *Eimeria* comprises a species of *Eimeria* that infects chickens.

13. The method of claim 1, wherein the *Eimeria* comprises a species of *Eimeria* that infects mammals.

14. A method of sporulating viable *Eimeria* oocysts, the method comprising: a. providing non-sporulated, viable *Eimeria* oocysts; b. contacting the non-sporulated viable *Eimeria* oocysts with a composition comprising a peroxygen compound and a combination of organic acids to effect sporulation, said composition having an acidic pH of less than pH 4 wherein the concentration of the peroxygen compound in the composition is from about 0.1% to about 10% (v/v) and the concentration of citric and propionic acids in the composition is from about 0.1% to about t 5%, and; wherein said method does not include the use of potassium dichromate.

* * * * *